(12) United States Patent
Zhang et al.

(10) Patent No.: US 9,506,900 B2
(45) Date of Patent: Nov. 29, 2016

(54) GAS TREATMENT DEVICE AND MEDICAL EQUIPMENT USING THE SAME

(71) Applicant: Shenzhen Mindray Bio-Medical Electronics Co., Ltd., Shenzhen (CN)

(72) Inventors: Xuegang Zhang, Shenzhen (CN); Zhonghua Liu, Shenzhen (CN); Meng Zhu, Shenzhen (CN); Weidong Zhou, Shenzhen (CN); Jian Cen, Shenzhen (CN); Shuangtao Xiong, Shenzhen (CN); Guangqi Huang, Shenzhen (CN); Joakim Carl Gabrielsson, Shenzhen (CN); Johan Nils Ernst Werner, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 316 days.

(21) Appl. No.: 14/334,435

(22) Filed: Jul. 17, 2014

(65) Prior Publication Data

US 2014/0326046 A1 Nov. 6, 2014

Related U.S. Application Data

(63) Continuation of application No. PCT/CN2012/087489, filed on Dec. 26, 2012.

(30) Foreign Application Priority Data

Jan. 19, 2012 (CN) .......................... 2012 1 0018137

(51) Int. Cl.
*B01D 53/02* (2006.01)
*G01N 33/00* (2006.01)
(Continued)

(52) U.S. Cl.
CPC ......... *G01N 33/0009* (2013.01); *A61B 5/0836* (2013.01); *A61M 16/0003* (2014.02);
(Continued)

(58) Field of Classification Search
CPC .......... A61B 5/0836; A61M 16/0003; A61M 16/01; A61M 16/085; A61M 16/104; A61M 2016/1025; A61M 2016/1035; A61M 2230/432; G01N 33/0006; G01N 33/0009; G05D 7/0635
See application file for complete search history.

(56) References Cited

U.S. PATENT DOCUMENTS 4,546,778 A 10/1985 Sullivan
5,616,923 A 4/1997 Rich et al.
(Continued)

FOREIGN PATENT DOCUMENTS

| CN | 101609089 A | 12/2009 |
|---|---|---|
| CN | 101784229 A | 7/2010 |
| CN | 201840743 U | 5/2011 |
| CN | 202010339 U | 10/2011 |
| CN | 102266619 A | 12/2011 |

*Primary Examiner* — Christopher P Jones
(74) *Attorney, Agent, or Firm* — Kory D. Christensen; Stoel Rives LLP

(57) ABSTRACT

Provided are gas treatment devices and medical equipment thereof. The gas treatment device can include at least a first gas monitoring module and a second gas monitoring module, a master control module and an integrated gas circuit board. A gas outlet, at least one gas inlet and a monitoring interface can be arranged on a surface of the integrated gas circuit board, while a first and a second gas circuits may be arranged inside the integrated gas circuit board. The gas inlet can include a first gas inlet and a second gas inlet. The gas outlet and the first gas inlet can communicate with first and second ends of the first gas circuit, and the second gas inlet can communicate with one end of the second gas circuit. The first and the second gas circuits can communicate with the first and the second gas monitoring modules through corresponding monitoring interfaces.

12 Claims, 4 Drawing Sheets

(51) Int. Cl.
*A61M 16/08* (2006.01)
*A61M 16/00* (2006.01)
*G05D 7/06* (2006.01)
*A61B 5/083* (2006.01)
*A61M 16/01* (2006.01)
*A61M 16/10* (2006.01)

(52) U.S. Cl.
CPC ........ *A61M16/085* (2014.02); *G01N 33/0006* (2013.01); *G05D 7/0635* (2013.01); *A61M 16/01* (2013.01); *A61M 16/104* (2013.01); *A61M 2016/1025* (2013.01); *A61M 2016/1035* (2013.01); *A61M 2230/432* (2013.01)

(56) References Cited

U.S. PATENT DOCUMENTS

| | | | |
|---|---|---|---|
| 2008/0142019 A1* | 6/2008 | Lewis | A61M 16/0666 128/207.18 |
| 2009/0062673 A1* | 3/2009 | Scampoli | A61B 5/087 600/529 |
| 2010/0294021 A1* | 11/2010 | Makino | G01N 25/18 73/25.03 |
| 2011/0100362 A1* | 5/2011 | Baecke | A61M 16/12 128/203.12 |
| 2011/0155131 A1* | 6/2011 | Bottom | A61M 16/104 128/203.14 |
| 2015/0075522 A1* | 3/2015 | Acker | A61M 16/0051 128/202.22 |

* cited by examiner

GAS TREATMENT DEVICE AND MEDICAL EQUIPMENT USING THE SAME

CROSS-REFERENCE

This application is a continuation of Patent Cooperation Treaty Application No. PCT/CN2012/087489, filed Dec. 26, 2012, which is hereby incorporated by reference.

TECHNICAL FIELD

This disclosure relates generally to medical equipment and particularly to gas treatment devices and medical equipment using the same.

BACKGROUND

During medical treatments, a gas concentration monitoring module for anesthetic gas and carbon dioxide ($CO_2$) may often be used to monitor an anesthetic gas concentration and a $CO_2$ concentration in a gas sample extracted from a patient. Specifically, an anesthetic gas monitoring (GMB) probe may be arranged in a gas sampling circuit for anesthetic gas in the gas concentration monitoring module for anesthetic gas and $CO_2$. When the anesthetic gas enters into the gas concentration monitoring module through the gas sampling circuit, the GMB probe can monitor the anesthetic gas concentration and the $CO_2$ concentration as needed.

In clinical practice, some other gas treatments may also be needed in addition to the monitoring of the anesthetic gas concentration and the $CO_2$ concentration. For example, an oxygen concentration monitoring module may be utilized for oxygen concentration monitoring, or a respiratory mechanics module may be used for monitoring respiratory mechanics parameters including pressure and differential pressure of the gas. In such case, the gas concentration monitoring module for anesthetic gas and $CO_2$ should be configured to coordinate with any other gas treatment modules. Gas circuits may also need to be connected when necessary. For example, a hose may be used for connecting the gas sampling circuit for anesthetic gas in the gas concentration monitoring module for anesthetic gas and $CO_2$ with an oxygen sampling circuit in the oxygen concentration monitoring module. All these may lead to complicated structure, bulky equipment size and inconvenient operation.

SUMMARY OF THIS DISCLOSURE

This disclosure provides gas treatment devices that can simplify connection structures for gas circuits and can be integrated with a variety of gas treatment functions.

In one aspect, a gas treatment device can include at least one first gas monitoring module, at least one second gas monitoring module, a master control module and an integrated gas circuit board. The master control module can be coupled to the first and the second gas monitoring modules to control these two gas monitoring modules.

A gas outlet, at least one gas inlet and at least one monitoring interface can be arranged on a surface of the integrated gas circuit board, where the gas inlet may include a first gas inlet and a second gas inlet. A first gas circuit and at least one second gas circuit may also be arranged inside the integrated gas circuit board. The first gas circuit may be a through passage with both inlet and outlet, while the second gas circuit may be a blind passage with one open end. The first gas inlet and the gas outlet can communicate with the two ends (e.g., first and second ends) of the first gas circuit, and the first gas circuit can communicate with the first gas monitoring module through the monitoring interface. The second gas inlet can communicate with the open end of the second gas circuit, and the second gas circuit can communicate with the second gas monitoring module through the monitoring interface.

In some embodiments, the gas treatment device may further include a circuit board. The master control module can be mounted on the circuit board. The circuit board and the integrated gas circuit board may be designed as a laminated structure, and the circuit board can be disposed on a surface of the integrated gas circuit board where the monitoring interface is arranged.

In some embodiments, the gas treatment device can further include at least one three-way valve communicating with the master control module through signals, at least one zero-calibration interface arranged on the surface of the integrated gas circuit board and a zero-calibration gas circuit arranged inside the integrated gas circuit board. Each three-way valve can have a zero-calibration end. The zero-calibration gas circuit may be a blind passage with one open end. The gas inlet can also include a zero-calibration gas inlet, and a gas inlet end of the zero-calibration gas circuit can communicate with the zero-calibration gas inlet. The zero-calibration gas circuit can communicate with the zero-calibration end of each three-way valve through the zero-calibration interface, and can controllably communicate with a portion of the first gas circuit in communication with the first gas monitoring module or with a portion of the second gas circuit in communication with the second gas monitoring module through the three-way valve.

In some embodiments, each three-way valve can further have a first connection end and a second connection end. The first connection end and the second connection end can be in constant communication with each other, and the zero-calibration end can communicate with the second connection end in the state of zero calibration.

In some embodiments, the first gas circuit and the second gas circuit may be respectively divided into a front section and a rear section along a gas flow direction. A first three-way valve interface and a second three-way valve interface respectively communicating with the front section and the rear section can be disposed on a surface of the integrated gas circuit board. The first three-way valve interface may communicate with the first connection end of each three-way valve, and the second three-way valve interface may communicate with the second connection end of each three-way valve. The zero-calibration interface, the first three-way valve interface and the second three-way valve interface that are connected to a same three-way valve can be arranged along a same straight line.

In some embodiments, the gas treatment device can include multiple three-way valves. The multiple three-way valves can be arranged side by side on the circuit board. The integrated gas circuit board may be pressed, i.e., press-fit, with the three-way valves, and the zero-calibration interface, the first three-way valve interface and the second three-way valve interface may be in alignment with the zero-calibration end, the first connection end and the second connection end of each three-way valve, respectively.

In some embodiments, the gas treatment device may further include at least one gas pump unit. The first gas circuit can also include two gas containers, and the gas pump unit may be connected between the two gas containers.

In some embodiments, the gas treatment device may include two gas pump units that may be connected to each other in parallel.

In some embodiments, the first gas monitoring module can be a gas concentration monitoring module, and the second gas monitoring module can be a respiratory mechanics monitoring module that includes a pressure sensor and a differential pressure sensor.

In some embodiments, the gas treatment device can include two second gas circuits that are independent from each other. The monitoring interface communicating with the second gas circuits can include a pressure sensor interface and two differential pressure sensor interfaces. The pressure sensor interface can communicate with one second gas circuit, and the pressure sensor may be press-fit with the pressure sensor interface. The differential pressure sensor interfaces may include a first differential pressure sampling port and a second differential pressure sampling port that can communicate with the two second gas circuits, and the differential pressure sensor may be press-fit with the differential pressure sensor interface.

In some embodiments, the gas treatment device can include multiple first gas monitoring modules that can be successively connected to the first gas circuit through corresponding monitoring interfaces.

In some embodiments, the first gas monitoring modules can include an oxygen concentration monitoring module and a gas concentration monitoring module for anesthetic gas and $CO_2$.

In some embodiments, the first gas monitoring module can include an external first gas monitoring module or an internal first gas monitoring module. The monitoring interface communicating with the first gas circuit may correspondingly include an external gas inlet interface and an external gas outlet interface that are connected to the external first gas monitoring module, and/or an internal gas inlet interface and an internal gas outlet interface that are connected to the internal first gas monitoring module. The external gas inlet interface and the external gas outlet interface or the internal gas inlet interface and the internal gas outlet interface may be selectively connected by a pipeline.

In some embodiments, the gas treatment device may further include a third gas circuit that may be arranged inside the integrated gas circuit board and be arranged with a gas flow limiter. The gas inlet can also include a negative pressure gas inlet, and the negative pressure gas inlet and the gas outlet can communicate with the first and second of the third gas circuit.

In another aspect, a gas treatment device can include multiple first gas monitoring modules and an integrated gas circuit board. The integrated gas circuit board may include a gas outlet, a first gas inlet and multiple monitoring interfaces arranged on a surface of the integrated gas circuit board. A first gas circuit can also be arranged inside the integrated gas circuit board. The first gas circuit may be a through passage with gas inlet/outlet. The first gas inlet and the gas outlet can communicate with the two ends of the first gas circuit, respectively, and the multiple first gas monitoring modules can be successively connected to the first gas circuit through corresponding monitoring interfaces.

In yet another aspect, a medical equipment can include the above-described gas treatment devices.

In some embodiments, the medical device can be an anesthesia device or a monitoring device.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The following detailed description of embodiments and this disclosure can be understood when combined with the figures, in which the same structure is represented by the same reference sign. In the figures.

DETAILED DESCRIPTION

Figure 1:
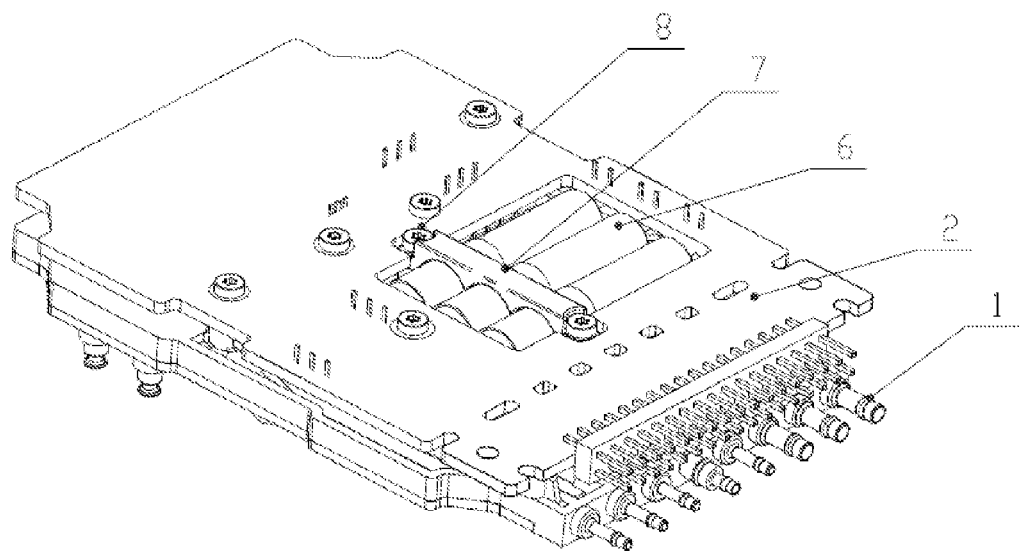
FIG. 1 is an assembly diagram for a gas treatment device according to an embodiment of this disclosure.

This disclosure is described in further detail below with reference to the figures and specific embodiments.

Gas treatment devices in this disclosure can provide guidance in a gas flow direction through gas circuits in an integrated gas circuit board. In this case, the gas to be monitored can be in natural circulation and/or be sampled in real time, and at least two kinds of gas treatments can be performed on the gas thereafter. For instance, some gas treatments such as concentration monitoring, mechanics parameter monitoring and/or negative pressure processing may be performed on the measured gas as required. Through such gas treatment devices, a simplified gas circuit structure can be achieved, and the gas circuits can be conveniently connected by effectively reducing the usage of hose for gas circuit connection.

In one embodiment, a gas treatment device can include at least one first gas monitoring module, at least one second gas monitoring module, a master control module and an integrated gas circuit board. The master control module may be coupled to the first and the second gas monitoring modules to control these two gas monitoring modules. A gas outlet, at least one gas inlet and at least one monitoring interface can be disposed on a surface of the integrated gas circuit board, while a first gas circuit and at least one second gas circuit can be disposed inside the integrated gas circuit board. The gas inlet may have a first gas inlet and a second gas inlet. The first gas circuit may be a through passage with both inlet and outlet, where the first gas inlet and the gas outlet can communicate with first and second ends of the first gas circuit to form an interconnected gas pathway, and the first gas circuit can communicate with the first gas monitoring module through the monitoring interface. In this case, the gas to be monitored can flow into the first gas circuit through the first gas inlet under the action of a gas pump, can be monitored by the first gas monitoring module and may then flow out of the gas outlet, thereby achieving real-time gas sampling by the first gas circuit. The second gas circuit may be a blind passage with one open end. The second gas inlet can communicate with the open end of the second gas circuit, and the second gas circuit can communicate with the second gas monitoring module through the monitoring interface. In this case, the gas to be monitored can flow into the second gas circuit through the second gas inlet and can then be monitored by the second gas monitoring module, so that the gas within the second gas circuit can be prevented from communicating with and being interference by external gas flow.

In an implementation, a main body of the gas treatment device may be configured as a laminated structure. The gas treatment device can include a circuit board and the integrated gas circuit board where the two boards are laminated to each other. The circuit board may be disposed on a surface of the integrated gas circuit board where the monitoring interface is arranged. The master control module can be mounted on the circuit board, while a power supply circuit, a signal processing circuit, a signal sampling and sensing module and the like can also be incorporated onto the circuit board for realizing system power supply, signal sampling, data calculation, data output etc. The mutually laminated arrangement between the circuit board and the integrated gas circuit board can lead to a more compact device structure, thereby reducing both size and power consumption of the gas treatment device. In order to further reduce an overall size of the device used for realizing multifunctional measurements, other gas treatment module(s) or device(s), such as sensor, oxygen concentration monitoring module and three-way valve, can also be affixed to the integrated gas circuit board or the circuit board. Each gas monitoring module may be provided with a signal interface and a gas circuit interface, where the signal interface can communicate with the master control module through signals. Here, wired or wireless connection can be used between the signal interface and the master control module, i.e., information interaction can be realized between the signal interface and the master control module through wired or wireless communication mode. The gas circuit interface may be engaged (e.g., sealed) to the corresponding monitoring interface of the integrated gas circuit board so as to implement the corresponding gas treatment.

In another embodiment, the gas treatment device may include multiple gas monitoring modules and an integrated gas circuit board. A gas outlet, a first gas inlet and multiple monitoring interfaces can be disposed on a surface of the integrated gas circuit board, and a first gas circuit, which may be a through passage with both inlet and outlet, can be disposed inside the integrated gas circuit board. The first gas inlet and the gas outlet can communicate with the two ends of the first gas circuit, respectively, to form an interconnected gas pathway, and the multiple gas monitoring modules can successively communicate with the first gas circuit through the corresponding monitoring interfaces. In this case, the gas to be monitored can first flow into the first gas circuit through the first gas inlet under the action of a gas pump and then flow out of the gas outlet after being monitored by the multiple first gas monitoring modules successively.

In the above-described embodiments, the integrated gas circuit board may be a board-shaped member made of metal or plastic. For example, two boards with recesses can be fixed together via ultrasonic welding, laser welding or bonding to form the integrated gas circuit board. In this approach, the gas circuits can be constructed by combining the corresponding recesses on the two boards. Alternatively, sealing material can be filled between the two boards to form the gas circuits.

Figure 2:
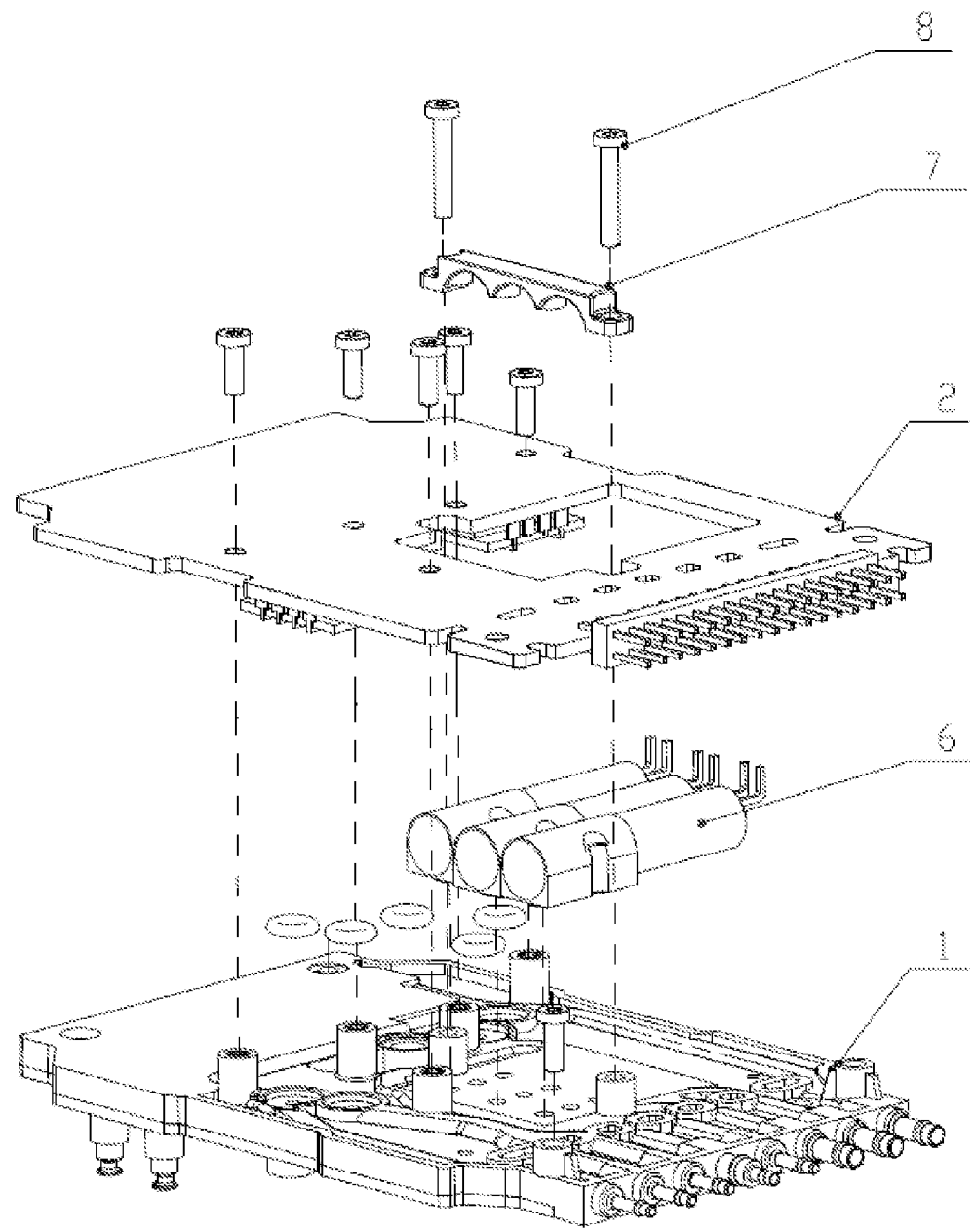
FIG. 2 is an exploded structure diagram for a gas treatment device according to an embodiment of this disclosure.
Figure 3:
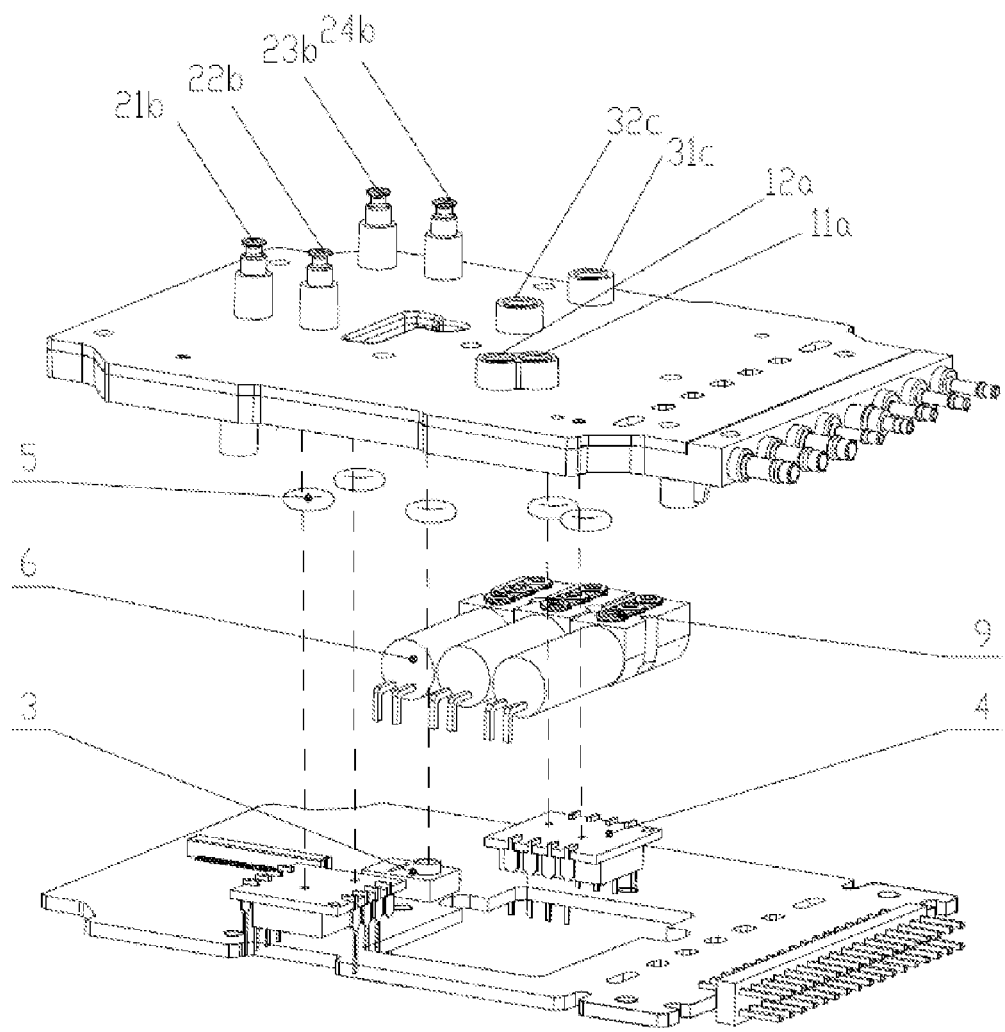
FIG. 3 is an exploded structure diagram for a gas treatment device from another view, according to an embodiment of this disclosure.

Referring to FIGS. 1-3, a gas treatment device in this embodiment is employed in medical equipment for gas treatment operations in a patient's breathing circuit. For instance, the gas treatment device can be used for gas concentration monitoring, respiratory mechanics parameter monitoring and the like. According to specific requirement, the gas treatment device may also perform negative pressure processing on the gas and then output negative pressure gas to any other devices. Specifically, a first gas monitoring module can include an oxygen concentration monitoring module and a gas concentration monitoring module for anesthetic gas and $CO_2$, where these two modules can be respectively used for monitoring an oxygen concentration as well as an anesthetic gas concentration and a $CO_2$ concentration. In other embodiments, the first gas monitoring module can also operate to monitor a concentration of another gas, and/or to monitor some other characteristics of the gas. A second gas monitoring module can be a respiratory mechanics monitoring module, which can include a pressure sensor for pressure monitoring and a differential pressure sensor for differential pressure monitoring. In an example, three basic parameters, namely airway pressure, airway flow and time, can be obtained by measuring the gas pressures at several points in an airway. Subsequently, respiratory mechanics parameters such as tidal volume, inspiration/expiration time (I:E) rate and positive end-expiratory pressure (PEEP) may be calculated to evaluate the ventilation condition within the patient's airway. In some other embodiments, the second gas monitoring module can also operate to monitor other characteristics of the gas.

In some embodiments, during gas concentration monitoring, differential pressure within the gas circuit(s) can further be measured by using the differential pressure sensor, and gas flow may then be calculated based on the differential pressure within the gas circuit(s), so that feedback information about the gas flow can be provided for gas flow control.

In some embodiments, an integrated gas circuit board 1 may be a metal board or a plastic board made by injection molding. Multiple gas inlets and one gas outlet can be arranged side by side on one end of the integrated gas circuit board 1. Monitoring interfaces for connecting to each gas monitoring module and other interfaces for connecting to devices such as a three-way valve 6 and a gas pump unit may be disposed on a surface of the integrated gas circuit board 1, while a gas container, a gas circuit flow limiter and multiple gas circuits may be disposed inside the integrated gas circuit board 1. In order to seal the gas circuits, a gas circuit interface of each gas monitoring module may be in sealed engagement with the monitoring interface on the surface of the integrated gas circuit board 1 by a sealing ring 5. A master control module on a circuit board 2 may communicate with each gas monitoring module and the three-way valve 6 through signals, and it may be deemed as a core control component of the whole system. Also, the circuit board 2 can be integrated with a hardware power supply circuit, a signal processing circuit and a signal sampling and sensing module that communicate with the master control module through signals. In this embodiment, for the purpose of space saving, a pressure sensor 3, a differential pressure sensor 4 and three three-way valves 6 for zero calibration may be affixed to the circuit board 2 through welding and/or bonding. Pins of all these devices can be welded to corresponding pins of the master control module. Through built-in sealing rings 9, the three-way valves 6 can also sealably connect to corresponding interfaces on the integrated gas circuit board 1. A press plate 7 can be pressed (e.g., press-fit) on the three three-way valves 6 arranged side by side, and the circuit board 2 can be fixed together with the integrated gas circuit board 1 by a screw 8 passing through the press plate 7. In this way, the whole device can become smaller and more compact in structure.

In some embodiments, the number and the mounting position of the three-way valve 6 can be flexibly arranged.

For example, it is possible that the number of the three-way valve 6 is the same as that of the gas circuit inside the integrated gas circuit board 1.

Figure 4:
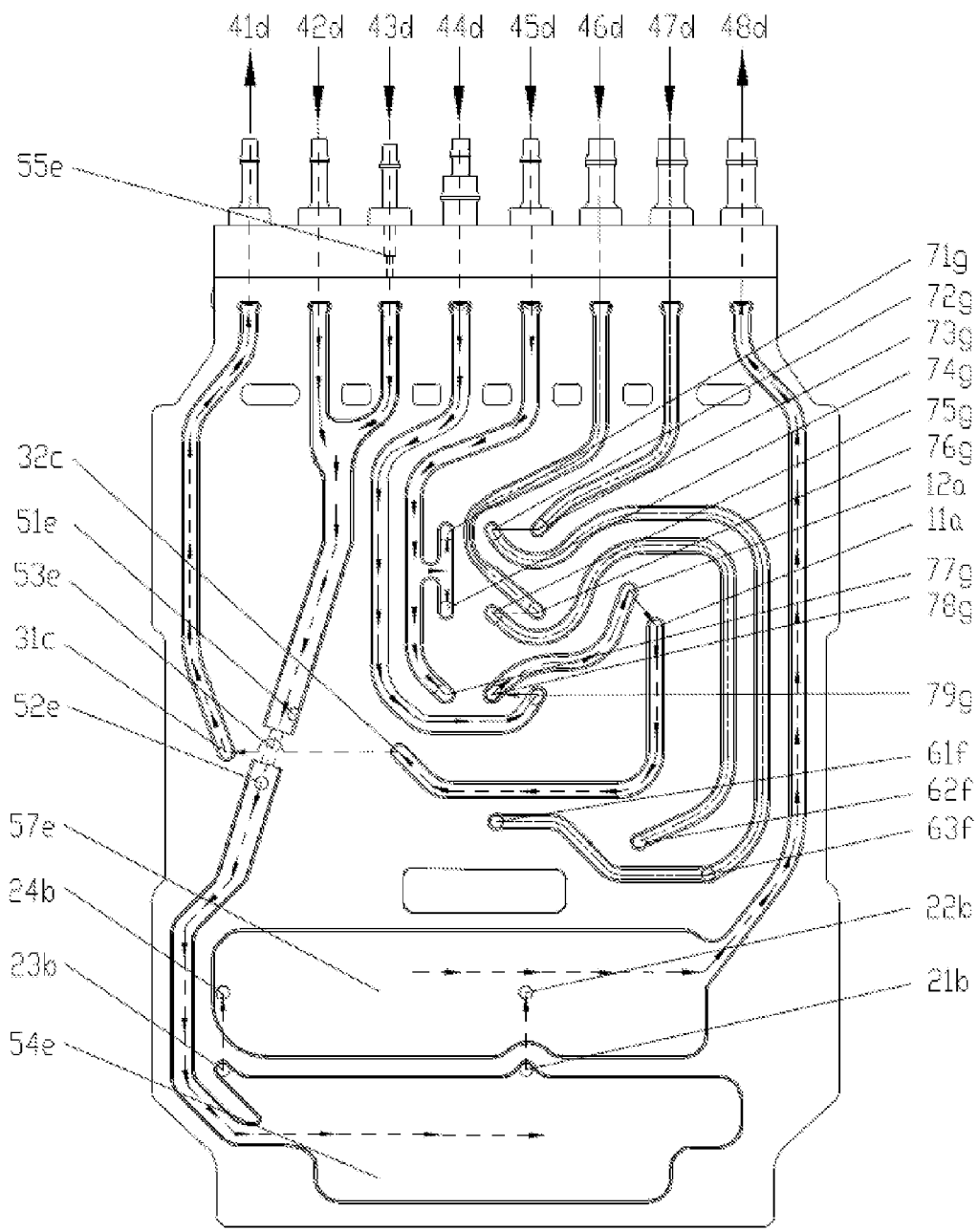
FIG. 4 is a schematic diagram illustrating flowing of gas in gas circuits inside an integrated gas circuit board according to an embodiment of this disclosure.

Referring to FIGS. 3 and 4, the gas inlets at the end of the integrated gas circuit board 1 may include a negative pressure gas inlet 43*d*, a first gas inlet 44*d*, a zero-calibration gas inlet 45*d* and two second gas inlets 46*d*, 47*d*. A gas pump may be required to make the gas flowing into the negative pressure gas inlet 43*d*, the first gas inlet 44*d* and the zero-calibration gas inlet 45*d* flow within corresponding gas circuits and flow out of a gas outlet 48*d*.

The gas circuits inside the integrated gas circuit board 1 may mainly include a first gas circuit, a second gas circuit, a third gas circuit and a zero-calibration gas circuit. The first gas circuit here is a gas sampling circuit. Since the gas in a patient's breathing circuit should be sampled in real time for the purpose of monitoring the gas concentration in the patient's breathing circuit, the first gas circuit should be a through gas-flow passage, and its inlet and outlet can communicate with the first gas inlet 44*d* and the gas outlet 48*d* of the integrated gas circuit board 1, respectively. As shown in FIG. 4, the dashed lines with arrows represent the first gas circuit, which can make the oxygen concentration monitoring module and the gas concentration monitoring module for anesthetic gas and $CO_2$ communicate with the first gas circuit in series, so that the oxygen concentration monitoring module and the gas concentration monitoring module for anesthetic gas and $CO_2$ can perform their respective gas concentration monitoring after successively extracting some gas samples from the first gas circuit. The gas circuit interface for the gas concentration monitoring module for anesthetic gas and $CO_2$ can be a group of GMB probes, and their corresponding monitoring interfaces on the surface of the integrated gas circuit board 1 can include a GMB gas inlet 12*a* and a GMB gas outlet 11*a*. The oxygen concentration monitoring module can be selected from an internal or an external oxygen concentration monitoring module based on the size requirement. In different situations, the corresponding monitoring interface on the surface of the integrated gas circuit board 1 can be an external gas inlet interface 41*d* and an external gas outlet interface 42*d* for connecting to an external oxygen concentration monitoring module; alternatively, the corresponding monitoring interface on the surface of the integrated gas circuit board 1 can be an internal gas inlet interface 32*c* and an internal gas outlet interface 31*c* for connecting to an internal oxygen concentration monitoring module. The external gas inlet interface 41*d* and the external gas outlet interface 42*d* (or the internal gas inlet interface 32*c* and the internal gas outlet interface 31*c*) can selectively communicate with each other by using gas pipelines. In order to reduce the size of the device and facilitate the gas circuit connection, the external gas inlet interface 41*d* and the external gas outlet interface 42*d* can be arranged side by side with respect to the multiple gas inlets and the gas outlet 48*d* of the integrated gas circuit board 1. In some embodiments, the multiple first gas monitoring modules for any other gas monitoring can further be connected to the first gas circuit in series through the corresponding monitoring interfaces. Similarly, one or more of these first gas monitoring modules may be internally or externally configured. Moreover, following the embodiments described above, these first gas monitoring modules can be selectively connected between the external gas inlet interface 41*d* and the external gas outlet interface 42*d* or between the internal gas inlet interface 32*c* and the internal gas outlet interface 31*c*.

The second gas circuit indicated by the dashed lines in FIG. 4, which is separated from the gas sampling circuit, may include two independent respiratory mechanics gas circuits. When monitoring the respiratory mechanics parameter(s) in the patient's breathing circuit, the ventilation condition inside the breathing circuit should be simulated, so as to measure the pressure and the differential pressure. In this embodiment, the second gas circuit may be a blind passage with one gas inlet end, and the second gas circuit may communicate with the breathing circuit. As a result, external gas flow(s) may not interfere with the second gas circuit, and no additional gas flow fluctuations can be formed in the second gas circuit. The monitoring interface on the surface of the integrated gas circuit board 1, which can be arranged to communicate with the respiratory mechanics gas circuit, may include a pressure sensor interface 61*f* and two differential pressure sensor interfaces. The pressure sensor interface 61*f* may communicate with one respiratory mechanics gas circuit, the pressure sensor 3 may be press-fit with the pressure sensor interface 61*f*, and a gas circuit interface of the pressure sensor 3 may be sealingly engaged with the pressure sensor interface 61*f*. The differential pressure sensor interface can be comprised of a first differential pressure sampling port 62*f* and a second differential pressure sampling port 63*f*, where the two differential pressure sampling ports can communicate with corresponding respiratory mechanics gas circuits. The differential pressure sensor 4 may be press-fit with the two differential pressure sensor interfaces, and their gas circuit interfaces may be also sealingly engaged with the two differential pressure sensor interfaces. In some embodiments, the second gas circuit may have at least three independent respiratory mechanics gas circuits that can be connected by corresponding monitoring interfaces to the multiple second gas monitoring modules for any other gas monitoring.

The third gas circuit can be a negative pressure gas circuit 55*e* that is provided with a flow limiter for negative pressure gas circuit 55*e*. In order to perform the negative pressure processing on the gas and then output the negative pressure gas to any other devices, the negative pressure gas inlet 43*d* with the gas outlet 48*d* may enter into communication with the negative pressure gas circuit 55*e*. In this embodiment, the negative pressure gas circuit 55*e* and the gas sampling circuit may have shared parts.

The gas treatment device may also include a gas pump unit, and the gas sampling circuit can include a first gas container 54*e* and a second gas container 57*e* to ensure stable pressure at a gas outlet of the gas pump unit. The gas pump unit can be connected between the two gas containers for achieving gas purging. The two gas containers and the gas pump unit can be shared by the negative pressure gas circuit 55*e* and the gas sampling circuit. Two gas pump units that are arranged in parallel may be provided in this embodiment, where each gas pump unit may have one or more gas pumps for extracting the gas from the first gas container 54*e* to the second gas container 57*e*. The gas extracted by the two gas pump units may form complementary gas flow to further improve the stability of the gas flow. The first gas pump unit may be connected to a first group of gas pump interfaces 21*b*, 22*b* on the surface of the integrated gas circuit board 1, and the second gas pump unit may be connected to a second group of gas pump interfaces 23*b*, 24*b* on the surface of the integrated gas circuit board 1. Based on actual needs, one or more gas pump units can further be connected between the first gas container 54*e* and the second gas container 57*e*.

The zero-calibration gas circuit shown by the arrows in FIG. 4 may be a blind passage with one open end. Each three-way valve 6 may have a zero-calibration end, a first connection end and a second connection end. The first connection end and the second connection end can be in constant communication with each other, while the zero-calibration end may communicate with the second connection end in the state of zero calibration. At least one zero-calibration interface can be disposed on the surface of the integrated gas circuit board 1, and the gas inlet of the integrated gas circuit board 1 may further include a zero-calibration gas inlet 45*d*, which can communicate with a gas inlet end of the zero-calibration gas circuit. The zero-calibration gas circuit can communicate with the zero-calibration ends of each three-way valve 6 through the zero-calibration interfaces. Also, following the instructions from the master control module, the zero-calibration gas circuit can controllably communicate with a portion of the gas sampling circuit in communication with the oxygen concentration monitoring module and the gas concentration monitoring module for anesthetic gas and $CO_2$, or with a portion of the respiratory mechanics gas circuit(s) in communication with the pressure sensor 3 or the differential pressure sensor 4. During zero calibration, standard gas may enter the gas sampling circuit or the respiratory mechanics gas circuit(s) through the zero-calibration gas inlet 45*d*, so that the zero-calibration operation can be carried out in the corresponding gas monitoring modules to improve the accuracy during the gas monitoring.

Since one gas sampling circuit and two respiratory mechanics gas circuits are provided in this embodiment, the zero-calibration gas circuit in the integrated gas circuit board 1 may have three zero-calibration interfaces. The gas sampling circuit and both the respiratory mechanics gas circuits may be divided into a front section and a rear section along the gas flow direction, where the oxygen concentration monitoring module and the gas concentration monitoring module for anesthetic gas and $CO_2$ may be connected at the rear section of the first gas circuit (i.e., the gas sampling circuit), and the pressure sensor 3 or the differential pressure sensor 4 may be connected at the rear section of the respiratory mechanics gas circuit. A first three-way valve interface and a second three-way valve interface respectively communicating with the front sections and the rear sections can further be disposed on the surface of the integrated gas circuit board 1. That is, the front section(s) of the gas sampling circuit or the respiratory mechanics gas circuits may communicate with one first three-way valve interface, and the rear section(s) of the gas sampling circuit or the respiratory mechanics gas circuits may communicate with one second three-way valve interface. Moreover, two three-way valve interfaces connected to the same gas circuit may be located adjacently. When the three-way valves 6 are connected to the gas sampling circuit or the respiratory mechanics gas circuits for gas circulation, the zero-calibration interface, the first three-way valve interface and the second three-way valve interface of a corresponding gas circuit can communicate with the zero-calibration end, the first connection end and the second connection end of the corresponding three-way valve 6. In this embodiment, the zero-calibration interface, the first three-way valve interface and the second three-way valve interface, which are arranged in a single gas circuit for connecting to the same three-way valve 6, can be arranged along the same straight line. The integrated gas circuit board 1 may also be press-fit with the three-way valves 6, while the zero-calibration interface, the first three-way valve interface and the second three-way valve interface may each be in alignment with the zero-calibration end, the first connection end and the second connection end of the three-way valve 6. In this way, the gas circuit can be more compact in structure and the size of the device can be further reduced.

In the gas sampling circuit, the first three-way valve interface 79*g* and the second three-way valve interface 78*g* may be in constant communication with each other by respectively connecting to the first connection end and the second connection end of the first three-way valve 6. In the case of zero calibration, the first three-way valve 6 may cause the first three-way valve interface 79*g* and the second three-way valve interface 78*g* to be disconnected from each other, and further cause its zero-calibration end 77*g* to communicate with the second three-way valve interface 78*g*, so that the zero-calibration gas circuit can communicate with the gas sampling circuit. In the first respiratory mechanics gas circuit, the first three-way valve interface 76*g* and the second three-way valve interface 75*g* may be in constant communication with each other by respectively connecting to the first connection end and the second connection end of the second three-way valve 6. In the case of zero calibration, the second three-way valve 6 may cause the first three-way valve interface 76*g* and the second three-way valve interface 75*g* to be disconnected from each other, and further cause its zero-calibration end 74*g* to communicate with the second three-way valve interface 75*g* so that the zero-calibration gas circuit can communicate with the first respiratory mechanics gas circuit. Similarly in the second respiratory mechanics gas circuit, the first three-way valve interface 73*g* and the second three-way valve interface 72*g* may be in constant communication with each other by respectively connecting to the first connection end and the second connection end of the third three-way valve 6. In the case of zero calibration, the third three-way valve 6 may cause the first three-way valve interface 73*g* and the second three-way valve interface 72*g* to be disconnected from each other, and further cause its zero-calibration end 71*g* to communicate with the second three-way valve interface 72*g* so that the zero-calibration gas circuit can communicate with the second respiratory mechanics gas circuit.

In this embodiment, the gas may flow in the gas sampling circuit according to the following sequences:

The first gas inlet 44*d* (or the zero-calibration gas inlet 45*d* during the zero calibration)→the three-way valve 6→the GMB probe through the GMB gas inlet 12*a* and the GMB gas outlet 11*a*→the internal oxygen concentration monitoring module through the internal gas inlet interface 32*c* and the internal gas outlet interface 31*c* (or the external oxygen concentration monitoring module through the external gas inlet interface 41*d* and the external gas outlet interface 42*d*)→a flow limiter for gas sampling circuit 53*e* and the differential pressure sensors 51*e*, 52*e*→the first gas container 54*e*→the first gas pump unit through the first gas pump interfaces 21*b*, 22*b* and the second gas pump unit through the second gas pump interfaces 23*b*, 24*b*→the second gas container 57*e*→the gas outlet 48*d*.

In the gas circuits described above, in case the internal oxygen concentration monitoring module is employed, the external gas inlet interface 41*d* and the external gas outlet interface 42*d* should be connected by a hose; instead, the internal gas inlet interface 32*c* and the internal gas outlet interface 31*c* should be connected by a hose when choosing to use the external oxygen concentration monitoring module. Alternatively, such interfaces may be connected by a shorting gas circuit. The flow limiter for gas sampling circuit 53*e* can produce differential pressure in the first gas circuit, and the gas treatment device can calculate the gas flow by measuring the produced differential pressure. Specifically, two ends of the flow limiter may include differential pressure sensors 51e, 52e to measure the differential pressure of the gas. The measured result may then be transmitted to the master control module, which can calculate the gas flow and output it to a medical staff for reference.

The gas may flow in the negative pressure gas circuit 55e according to the following sequences:

The negative pressure gas inlet 43d→the flow limiter for negative pressure gas circuit 55e→the first gas container 54e→the first gas pump unit through the first gas pump interfaces 21b, 22b and the second gas pump unit through the second gas pump interfaces 23b, 24b→the second gas container 57e→the gas outlet 48d.

The first respiratory mechanics gas circuit may become communicatively coupled as follows:

The second gas inlet 46d (or the zero-calibration gas inlet 45d during the zero calibration)—the three-way valve 6—the differential pressure sensor through the first differential pressure sampling port 62f.

The second respiratory mechanics gas circuit may become communicatively coupled as follows:

The second gas inlet 46d (or the zero-calibration gas inlet 45d during the zero calibration)—the three-way valve 6—the differential pressure sensor through the second differential pressure sampling port 63f—the pressure sensor through the pressure sensor interface 61f.

The above-described gas treatment devices can be integrated with the gas circuits used for various gas treatments. These gas circuits are simply connected, and prevented from being connected through the hose, thereby realizing simple structure, convenient operation and reduced size of the gas treatment device. All the gas treatment processes may be controlled uniformly by the master control module of the gas treatment device, and a power supply circuit and a portion of sensors may be configured onto the master control module. As a result, the gas treatment device may be integrated in functionality and/or structure. Accordingly, the size, power consumption, and/or the cost of the gas treatment device can be significantly reduced and its operation can become more convenient and flexible.

The above-described gas treatment devices can be widely applied to medical equipment such as anesthesia equipment, monitoring equipment or any other gas treatment equipment. Due to its small size, high level of integration and simple connection structures among the gas circuits, the gas treatment device in various embodiments of this disclosure can be facilitated in clinical applications.

Based on the content of this disclosure, those skilled in the art should understand that two, three or more gas circuits can be selectively made in the integrated gas circuit board according to device requirements. All the gas circuits may be used simultaneously or selectively. For example, one or more components of the gas circuits may be used while the others may be closed or left unused. In some other embodiments, the gas circuits in the integrated gas circuit board can be made into two or three layers based on the thickness of the integrated gas circuit board.

This disclosure is described above as detailed illustrations with reference to specific implementations, however this disclosure should not be limited to these illustrations. For those of ordinary skill in the art, various conclusions or equivalents may be made without departing from the concept of this disclosure; such conclusions or equivalents should be deemed to be included within the scope of this disclosure.

The invention claimed is:

1. A gas treatment device, comprising:
a first gas monitoring module;
a second gas monitoring module;
a master control module respectively coupled to the first gas monitoring module and the second gas monitoring module to control said first and second gas monitoring modules; and
an integrated gas circuit board, wherein the integrated gas circuit board comprises:
a gas outlet, at least one gas inlet and at least one monitoring interface arranged on a surface of the integrated gas circuit board, wherein the gas inlet comprises a first gas inlet and a second gas inlet;
a first gas circuit arranged inside the integrated gas circuit board, wherein the first gas circuit is a through passage with both inlet and outlet, the first gas inlet and the gas outlet communicate with first and second ends of the first gas circuit, and the first gas circuit communicates with the first gas monitoring module through the monitoring interface; and
at least one second gas circuit arranged inside the integrated gas circuit board, wherein the second gas circuit is a blind passage with one open end, the second gas inlet communicates with the open end of the second gas circuit, and the second gas circuit communicates with the second gas monitoring module through the monitoring interface.

2. The gas treatment device of claim 1, further comprising a circuit board, wherein the master control module is mounted on the circuit board, the circuit board and the integrated gas circuit board are designed as a laminated structure, and the circuit board is disposed on a surface of the integrated gas circuit board where the monitoring interface is arranged.

3. The gas treatment device of claim 2, further comprising:
at least one three-way valve communicating with the master control module through signals, wherein each three-way valve has a zero-calibration end;
at least one zero-calibration interface arranged on a surface of the integrated gas circuit board;
a zero-calibration gas circuit arranged inside the integrated gas circuit board, wherein the zero-calibration gas circuit is a blind passage with one open end, the gas inlet also comprises a zero-calibration gas inlet, and a gas inlet end of the zero-calibration gas circuit communicates with the zero-calibration gas inlet, and the zero-calibration gas circuit communicates with the zero-calibration end of each three-way valve through the zero-calibration interface and controllably communicates with a portion of the first gas circuit in communication with the first gas monitoring module or with a portion of the second gas circuit in communication with the second gas monitoring module through the three-way valve.

4. The gas treatment device of claim 3, wherein:
each three-way valve further comprises a first connection end and a second connection end, wherein the first connection end and the second connection end are in constant communication with each other, and the zero-calibration end communicates with the second connection end in the state of zero calibration;
the first gas circuit and the second gas circuit are each divided into a front section and a rear section along a gas flow direction; a first three-way valve interface and a second three-way valve interface respectively communicating with the front section and the rear section are disposed on a surface of the integrated gas circuit board; the first three-way valve interface communicates with the first connection end of each three-way valve, and the second three-way valve interface communicates with the second connection end of each three-way valve; and the zero-calibration interface, the first three-way valve interface and the second three-way valve interface that are connected to a same three-way valve are arranged along a same straight line.

5. The gas treatment device of claim 4, wherein said at least one three-way valve comprises multiple three-way valves; the multiple three-way valves are arranged side by side on the circuit board; the integrated gas circuit board is press-fit with the three-way valves; and the zero-calibration interface, the first three-way valve interface and the second three-way valve interface are in alignment with the zero-calibration end, the first connection end and the second connection end of each three-way valve, respectively.

6. The gas treatment device of claim 1, further comprising at least one gas pump unit, wherein the first gas circuit also includes two gas containers, and the gas pump unit is connected between the two gas containers.

7. The gas treatment device of claim 6, wherein said at least one gas pump unit comprises two gas pump units that are connected to each other in parallel.

8. The gas treatment device of claim 1, wherein the first gas monitoring module is a gas concentration monitoring module, and the second gas monitoring module is a respiratory mechanics monitoring module comprising a pressure sensor and a differential pressure sensor;

said at least one second gas circuit comprises two second gas circuits that are independent from each other; the monitoring interface communicating with the second gas circuits comprises a pressure sensor interface and two differential pressure sensor interfaces; the pressure sensor interface communicates with one second gas circuit, and the pressure sensor is press-fit with the pressure sensor interface; the differential pressure sensor interfaces comprise a first differential pressure sampling port and a second differential pressure sampling port that communicate with the two second gas circuits; and the differential pressure sensor is press-fit with the differential pressure sensor interface.

9. The gas treatment device of claim 8, wherein said at least one first gas monitoring module comprises multiple first gas monitoring modules, and the multiple first gas monitoring modules are successively connected to the first gas circuit through corresponding monitoring interfaces.

10. The gas treatment device of claim 9, wherein the first gas monitoring modules comprise an oxygen concentration monitoring module and a gas concentration monitoring module for anesthetic gas and carbon dioxide.

11. The gas treatment device of claim 8, wherein the first gas monitoring module comprises an external first gas monitoring module or an internal first gas monitoring module; the monitoring interface communicating with the first gas circuit comprises an external gas inlet interface and an external gas outlet interface that are connected to the external first gas monitoring module, and/or an internal gas inlet interface and an internal gas outlet interface that are connected to the internal first gas monitoring module; and the external gas inlet interface and the external gas outlet interface or the internal gas inlet interface and the internal gas outlet interface are selectively connected by a pipeline.

12. The gas treatment device of claim 9, further comprising a third gas circuit arranged inside the integrated gas circuit board, wherein the third gas circuit is arranged with a gas flow limiter; the gas inlet also comprises a negative pressure gas inlet; and the negative pressure gas inlet and the gas outlet communicate with first and second ends of the third gas circuit, respectively.

* * * * *